US009220773B2

(12) United States Patent
Chirwa et al.

(10) Patent No.: US 9,220,773 B2
(45) Date of Patent: Dec. 29, 2015

(54) PHARMACEUTICAL COMPOSITION (75) Inventors: Nthato Chirwa, Johannesburg (ZA);
Viness Pillay, Johannesburg (ZA);
Yahya Essop Choonara, Johannesburg (ZA); Pradeep Kumar, Johannesburg (ZA); Lisa Claire Du Toit, Johannesburg (ZA)

(73) Assignee: UNIVERSITY OF THE WITWATERSRAND, JOHANNESBURG, Johannesburg (ZA)

( * ) Notice: Subject to any disclaimer, the term of this patent is extended or adjusted under 35 U.S.C. 154(b) by 104 days.

(21) Appl. No.: 13/988,968

(22) PCT Filed: Nov. 28, 2011

(86) PCT No.: PCT/IB2011/055332
§ 371 (c)(1),
(2), (4) Date: Sep. 10, 2013

(87) PCT Pub. No.: WO2012/070029
PCT Pub. Date: May 31, 2012

(65) Prior Publication Data
US 2014/0004185 A1    Jan. 2, 2014

(30) Foreign Application Priority Data

Nov. 26, 2010  (ZA) ....................... 10/3747

(51) Int. Cl.
*A61K 39/395* (2006.01)
*A61K 9/00* (2006.01)
*A61K 9/107* (2006.01)
*A61K 31/337* (2006.01)
*A61K 39/44* (2006.01)
*A61K 31/282* (2006.01)
*A61K 31/4745* (2006.01)
*A61K 9/51* (2006.01)
*A61K 47/48* (2006.01)
*C07K 16/30* (2006.01)
*A61K 9/127* (2006.01)

(52) U.S. Cl.
CPC ......... *A61K 39/39558* (2013.01); *A61K 9/0024* (2013.01); *A61K 9/1075* (2013.01); *A61K 9/1273* (2013.01); *A61K 9/5146* (2013.01); *A61K 9/5153* (2013.01); *A61K 31/282* (2013.01); *A61K 31/337* (2013.01); *A61K 31/4745* (2013.01); *A61K 39/44* (2013.01); *A61K 47/488* (2013.01); *C07K 16/3092* (2013.01)

(58) Field of Classification Search
CPC . A61K 9/0024; A61K 9/1075; A61K 9/1273; A61K 39/44; A61K 9/51; A61K 9/5153
See application file for complete search history.

(56) References Cited

U.S. PATENT DOCUMENTS

2004/0005647 A1* 1/2004 Denardo et al. ............. 435/7.23
2008/0260833 A1* 10/2008 Hirt et al. .................... 424/486

OTHER PUBLICATIONS

William E. Paul (Fundamental Immunology ed., 3d ed., p. 242, 1993).*
The Merck Veterinary Manual (http://www.merckmanuals.com/vet/appendixes/reference_guides/normal_rectal_temperature_ranges.html, Dec. 2, 2014).*
Raske et al. (J. Zoo and Wildlife Medicine 2012 43(3): 517-521).*
Jadhav et al. (Current Drug Therapy 2010 5(4): 250-261).*
Jiang et al. (Biomacromoles 2007, 8:3184-3192).*
Muthu et al. (Nanomedicine 2009 4(6): 657-667).*
Straubinger et al. (Cancer Research Sep. 15, 1988 48:5237-5245).*
Carter and Merchant (Curr. Opin. Biotech. 1997: 449-454).*
Xiao et al. (Cancer Res. Apr. 15, 2010 70(8): Suppl. 1 Abstract No. 3686).*
Gillespie et al. (Annals of Oncol. 2000 11:735-741).*
Chinese Office Action issued in Chinese Patent Application No. 2011800655385 on Jun. 19, 2014, (first page only).
Kufe, "Mucins in cancer: function, prognosis and therapy", Nature Reviews Cancer, vol. 9 (2009) pp. 874-885.
Moase et al., "Anti-MUC-1 immunoliposomal doxorubicin in the treatment of murine models of metastatic breast cancer", Biochimica et Biophysica Acta vol. 1510 (2001) pp. 43-55.
Supplementary European Search Report issued in European Patent Application No. 11 84 3359 on Aug. 8, 2014.
Ta et al., "Thermosensitive Liposomes Modified with Pily(N-isopropylacrylamide-co-propylacrylic acid) Copolymers for Triggered Release of Doxorubicin", Biomacromolecules, vol. 11 (2010) pp. 1915-1920.
Yallapu et al., "Scope of nanotechnology in ovarian cancer therapeutics", Journal of Ovarian Research, vol. 3, No. 19 (2010) pp. 1-10.

* cited by examiner

*Primary Examiner* — Peter J Reddig
(74) *Attorney, Agent, or Firm* — Birch, Stewart, Kolasch & Birch, LLP (57) ABSTRACT A pharmaceutical composition for intraperitoneal delivery of an anti-neoplastic agent is provided for treating cancers associated with aberrant mucin expression, preferably ovarian cancer and pancreatic, prostate, metastatic breast, bladder and lung cancers. The composition comprises nanomicelles loaded with the anti-neoplastic agent, and antibodies such as anti-MUC16, anti-MUC1 or anti-MUC4 are conjugated to these nanomicelles. The antibody-bound nanomicelles are optionally embedded in a biodegradable pH- and thermoresponsive hydrogel capable of sol-gel transition at body temperature. The pharmaceutical composition is implantable in the peritoneum, where it transforms into a semi-solid gel at the body's core temperature. In response to pH, the hydrogel swells and releases the antibody-bound nanomicelles. The nanomicelles specifically target mucin antigens on cancer cells. The anti-mucin antibodies can be internalized by the tumor cells, enabling the drug-loaded nanomicelles to gain entry and deliver the chemotherapeutic drugs inside the tumor cell.

23 Claims, 5 Drawing Sheets
(5 of 5 Drawing Sheet(s) Filed in Color)

V<sub>H</sub> ACA125 clone 3:

FW1								CDR1			FW2
QVKLQESGAELARPGASVKLSCKASGYTFT	NVWMQ		WVKQRPGQGLDWIG

CDR2						FW3
AFYPGDGNTRYTHKFKG	KATLTADKSSSTAYMQLSSLASEDSGVYYCAR

CDR3			FW3
GEGNYAWFAY		WGQGTTVTVSS

Linker: [Gly, Ser]₃

V<sub>L</sub> ACA125 clone 3:

FW1							CDR1			FW2				CDR2
DIELTQSPASLSASVGETVTITC		QASENIFSYLA		WHQQKQGKSPQLLVY		NAKTLAG

FW3								CDR3			FW4
GVSSRFSGSGSGTHFSLKIKSLQPEDFGIYYC	QHHYGILPT		FGGGTKLEIKR

PHARMACEUTICAL COMPOSITION

A computer readable form (CRF) of the Sequence Listing in full compliance with 37 C.F.R. §§1.821-1.825 has been filed. The CRF of the Sequence Listing file has the name "20150409SubSeqListing_05870109PUS1_ST25.txt" and was created on Apr. 9, 2015 and has the file size of 5.45 kb. The Sequence Listing file "20150409SubSeqListing_05870109PUS1_ST25.txt" is hereby incorporated in its entirety by reference.

FIELD OF THE INVENTION

The present invention relates to a pharmaceutical composition for the selective delivery of anti-neoplastic agents to cancer cells.

BACKGROUND TO THE INVENTION

Ovarian cancer (a highly metastatic and lethal gynaecologic malignancy) is a challenging disease to treat, and since it presents with few early symptoms it is usually diagnosed late when in advanced stages, i.e. stage III (tumour on one or both ovaries with intraperitoneal metastasis) or stage IV (tumour on one or both ovaries with distant metastases to the lungs and liver) (Feldman, 1989; Friedlander, 1998; Seiden, 2001; Auersperg et al., 2001; Whitehouse and Solomons, 2003).

The current treatment for ovarian cancer makes use of aggressive cyto-reductive surgery, chemotherapy and external beam radiotherapy (Hoskins et al., 1994; MacGibbon et al., 1999; Trimble et al., 2003). Post-operatively, intravenous (IV) chemotherapy of a taxane (such as paclitaxel) or a platinum agent (such as carboplatin), or a combination thereof, is administered (Cannistra, 2004). The vasculature supplying tumour tissue is hyper-permeable and this renders intravascular therapy a preferred method for the delivery of anti-neoplastic agents (Maeda et al., 2000). The absence of effective lymphatic drainage from tumour tissue contributes in sustaining drug exposure to tumour tissues (Shama et al., 1996). However, due to the poor bioavailability of systemically administered anti-neoplastic drugs, chemo-resistant-tumours arise (Yusuf et al., 2003). Doxorubicin (Doxil®) and albumin-bound paclitaxel (Abraxane®) liposomes are approved by the FDA for potential use in treatment of solid tumours. However, their size (150 and 130 nm, respectively) limits their effectiveness in drug delivery (Unezaki et al., 1996; Dreher et al., 2006). Despite several studies having demonstrated the benefits of using intraperitoneal (IP) administration over intravenous administration (Alberts et al., 1996; Markman et al., 2001; Armstrong et al., 2006), the use of intraperitoneal chemotherapy to improve treatment in post-operative ovarian cancer patients has yielded controversial clinical outcomes that discourage its use as a treatment option compared to intravenous chemotherapy (Dubbelman et al., 1988; Markman et al., 1992; Markman and Walker, 2006; Ozols et al., 2006; Swart et al., 2008).

Patients suffering from recurrent ovarian cancer undergo extensive chemotherapy, radiotherapy or a combination of the two as no effective curative therapy is currently available (Jacobs et al., 1992; Menon and Jacobs, 2002).

There is therefore a need for new compositions or methods for treating ovarian and related cancers which avoid at least some of the problems described above or which reduce chemoresistance or limit the rapid metastatic spread (intraperitoneally and distant) of ovarian cancer cells.

SUMMARY OF THE INVENTION

According to a first embodiment of the invention, there is provided a pharmaceutical composition for the delivery of an anti-neoplastic agent to the human or animal body, the composition comprising:
  nanoparticles comprising an anti-neoplastic agent; and
  mucin antibodies.

The mucin antibodies may be anti-MUC16, anti-MUC1 or anti-MUC4 antibodies.

The anti-MUC16 antibodies may be humanised antibodies CA125 or OC125, the anti-MUC1 antibodies may be humanised antibodies CTM01, CMB-401, EMA or CA15-3, and the anti-MUC4 antibodies may be humanised antibody 1G8.

The anti-neoplastic agent may be encapsulated within the nanoparticles.

The nanoparticles may be nanomicelles, which may be less than about 100 nm in diameter.

The nanomicelles may be formed from poly(3-benzyl-1-glutamate), P poly(glutamic acid), poly(-benzyl-1-glutamate) and polyethylene glycol or bovine serum albumin.

The antibodies may be conjugated to the nanomicelles.

The anti-neoplastic agent may be paclitaxel, SN-38 (7-ethyl-10-hydroxy-camptothecin), carboplatin, oxaliplatin, cisplatin, ceramide, calcheamicin or carboxyamido-triazole, or any combination thereof.

The nanomicelles may be encapsulated in a thermal- and pH-responsive hydrogel composition which is liquid at about ambient room temperature and in a solid or semi-solid form at body temperature and which swells in an acidic environment and thereby releases the nanomicelles.

The hydrogel composition may be formed from one or more of the biodegradable polymers selected from the group consisting of N-isopropylacrylamide (NIPAAM), 2-(dimethylamino)ethyl methacrylate (DMAEMA) and poly(methacrylic acid) (PMAA).

The hydrogel composition may be additionally formed from chitosan, gelatine and/or dextran.

The pharmaceutical composition may be for use in treating cancer, and preferably cancers associated with aberrant mucin expression, such as ovarian cancer, pancreatic, prostate, metastatic breast, bladder or lung cancers. Most preferably, the cancer is ovarian cancer.

The pharmaceutical composition may be in an injectible formulation, preferably for injection into the intraperitoneal cavity.

According to a second embodiment of the invention, there is provided a method of manufacturing a pharmaceutical composition substantially as described above, the method comprising the steps of:
  encapsulating at least one anti-neoplastic agent within nanomicelles;
  conjugating mucin antibodies to the nanomicelles; and
  incorporating the antibody-bound nanomicelles into a biodegradable pH- and thermo-responsive hydrogel composition.

According to a third embodiment of the invention, there is provided a method of treating cancer in a human or animal, the method comprising the steps of administering a therapeutically effective amount of a pharmaceutical composition substantially as described above to the human or animal.

The composition may be injected into the human or animal at a target site and form a semi-solid hydrogel in response to the body temperature, whereafter the hydrogel may swell in response to the pH of the surrounding fluid and release antibody-bound nanomicelles which specifically target mucin antigens on cancer cells and deliver the anti-neoplastic agents into the targeted cancer cells.

BRIEF DESCRIPTION OF THE FIGURES

The patent or application file contains at least one color drawing. Copies of this patent or patent application publication with color drawings will be provided by the USPTO upon request and payment of the necessary fee.

DETAILED DESCRIPTION OF THE INVENTION

One of the risk factors for developing ovarian cancer is age (Hankinson et al., 1995; Hempling et al., 1997; Rossing et al., 1994; Daly and Obrams, 1998). After menopause, the ovaries shrink and become folded (forming cysts lined with ovarian surface epithelial cells), creating a conducive environment for the development of epithelial ovarian cancer, the most common malignant form of ovarian cancer (Auersperg et al., 1998; 2001; 2002; Feeley and Wells, 2001; Ozols et al., 2004). Ovarian tumours exhibit diverse and altered cell surface antigens, such as HE4, CA72-4, EGFR, SMRP and mucin (MUC16), which discriminate them from normal ovary cells and other normal cells lining the peritoneum (Order et al., 1975; Knauff and Urbach, 1977; Stohlbach et al., 1979; Moore et al., 2007). MUC16, also referred to as CA125 (cancer antigen 125), is the most investigated cell surface antigen in ovarian cancer and because it is shed into the serum, it is widely used for diagnosing and managing epithelial ovarian cancer (Bast et al., 1981; Jacobs et al., 1992; Yin et al., 2002; Fritsche and Bast, 1998; Menon and Jacobs, 2002).

The term mucin refers to the high molecular mass glycoprotein responsible for the gel-forming properties of mucus. The mucin protein is encoded by mucin genes (designated MUC) which are named in the order of their discovery. To date, 21 MUC genes that encode the protein backbone of mucins have been identified (Hollingsworth and Swanson, 2004).

Figure 1:
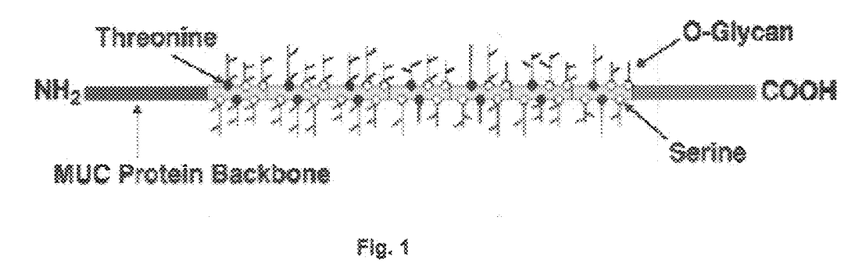
FIG. 1: is a diagrammatic representation of a mucin glycoprotein (encoded by a MUC gene).

Mucins are synthesized in epithelial cells within the human body and protect epithelial cells from infection and injury by maintaining their hydrated and lubricated surfaces (Gendler and Spicer, 1995). FIG. 1 is a diagrammatic representation of a mucin glycoprotein (encoded by a MUC gene) characterized by high serine and threonine residues on the protein backbone to which a high content of O-glycans are attached (Rose and Voynow, 2006). Cancer-associated mucins show aberrant or incomplete glycosylation. During malignant transformation, the glycosylation of the peptide backbone is altered, resulting in novel carbohydrate epitopes or the exposure of the peptide backbone (Hilgers et al., 1988). This change in mucin expression results in the loss of polarity of the epithelial cell, and the subsequent increase in synthesis results in large amounts of mucin being either shed or secreted by tumour cells for metastasis and adhesion, forming secondary tumour nodules (Hollingsworth et al., 1994; Singh et al., 2004; 2007; Yin et al., 2002).

In ovarian cancer, MUC1 has been shown to inhibit apoptosis, influence chemoresistance and promote metastasis of ovarian cancer cells (Dong et al., 1997; Tamada et al., 2007). MUC4 is expressed in the early stages of ovarian cancer and its potential use as a biomarker for early diagnosis is being explored (Giuntoli et al., 1998; Chauhan et al., 2006; Davidson et al., 2007). MUC16, a serum marker for ovarian cancer, has been shown to facilitate the immune escape of ovarian cancer cells (Patankar et al., 2005; Murdoch et al., 2006; Belisle et al., 2007; Gubbels et al., 2010).

The present invention provides a pharmaceutical composition for intraperitoneal delivery of one or more anti-neoplastic or chemotherapeutic agents, typically a combination of taxanes and platinum analogues, for treating cancers associated with aberrant mucin expression, preferably ovarian cancer and those from among the group of pancreatic, prostate, metastatic breast, bladder and lung cancers. The pharmaceutical composition comprises polymeric nanoparticles, typically nanomicelles, loaded with the anti-neoplastic agent(s). Mucin antibodies, such as anti-MUC16, anti-MUC1 or anti-MUC4, are bound to these nanomicelles. Suitable nanomicelles anti-neoplastic drugs include a combination of paclitaxel and carboplatin, altretamine, cisplatin, ceramide, calcheamicin, carboxyamido-triazole and the like.

The antibody-bound nanomicelles are optionally embedded in a biodegradable pH- and thermo-sensitive hydrogel capable of sol-gel transition at body temperature, and the composition is implantable in the peritoneum. The hydrogel composition may be formed from one or more biodegradable polymers selected from the group consisting of N-isopropylacrylamide (NIPAAM) (a temperature-sensitive monomer), 2-(dimethylamino)ethyl methacrylate (DMAEMA) and poly (methacrylic acid) (PMAA) (pH-sensitive monomers).

The use of MUC1, MUC4 and/or MUC16 allows for specific targeting of epithelial cancer cells expressing mucin antigens on their surfaces. It is important to note that the surface epithelium of ovaries is the only region in the ovaries that expresses mucins (Auersperg et al., 2001; Lynch et al., 1998) and because most ovarian cancers are of epithelial origin, mucins are the attractive targets in the delivery of anti-neoplastic drugs. The change in mucin expression during the transformation of normal ovarian surface epithelium to cancer is an important step towards disease progression. It has been shown that ovarian cancer cells that express MUC16 have an additional advantage to escape immune surveillance (Belisle et al., 2007; Murdoch et al., 2006; Patankar et al., 2005). This advantage enables ovarian cancer cells to interact and adhere to the visceral mesothelium (mesothilial cells) lining the peritoneum and organs found in the abdomen (stomach, large intestine, small intestine and kidneys) so that secondary tumour sites can be successfully established (Gubbels et al., 2006; Rump et al., 2004).

Figure 2:
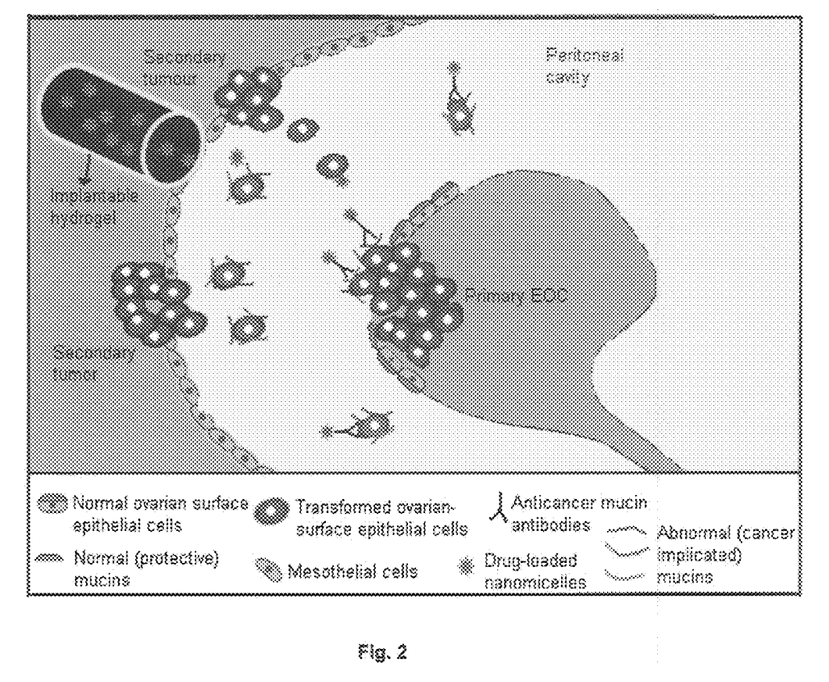
FIG. 2: illustrates a mechanism of action of the invention.
Figure 3:
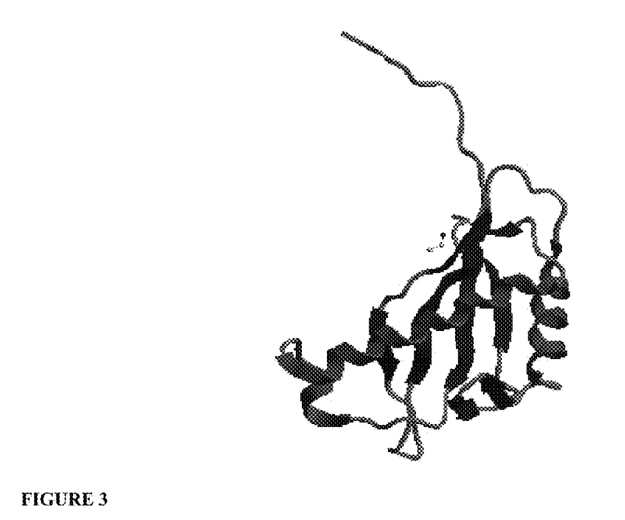
FIG. 3: shows a computer-generated model of the 3-dimensional folded structure of MUC16 protein (generated on ChemBio3D Ultra—loaded from Protein Data Bank).
Figure 4:
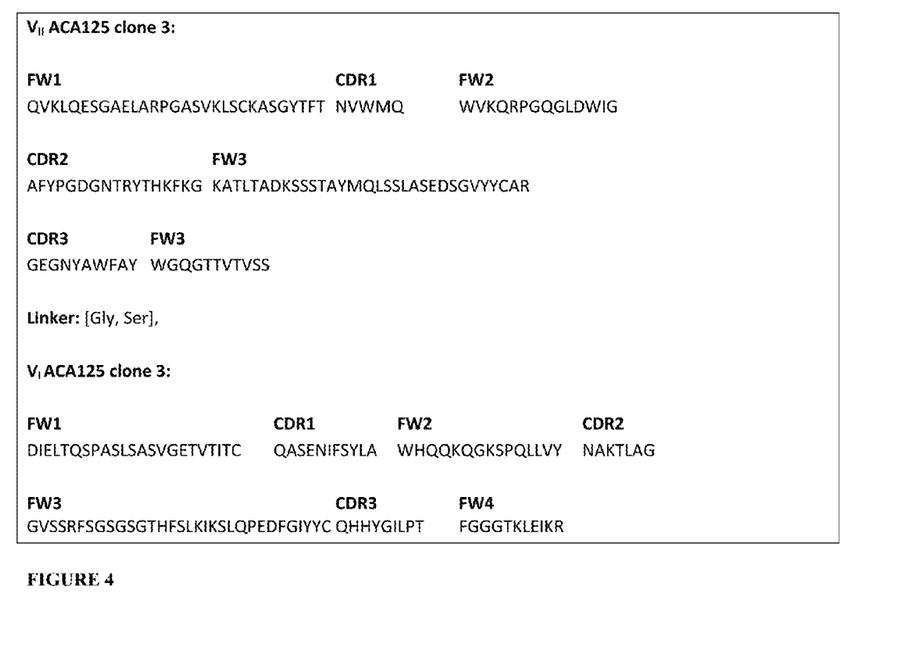
FIG. 4: shows a schematic of the amino acid sequence (SEQ ID NO: 2-15).

FIG. 2 illustrates a mechanism of action of the composition of the present invention. Once injected into the peritoneal cavity, the hydrogel transforms into a semi-solid gel by the body's core temperature. In response to the pH of the peritoneal fluid (acidic in infected patients and neutral in non-infected), the hydrogel swells and releases the antibody-bound nanomicelles. The nanomicelles (formulated to circulate for a long time in the peritoneal fluid) specifically target mucin 1, 4 and/or 16 antigens significantly over-expressed on cancer cells at the primary tumour site (tumour confined to the ovary in stage I and stage II), those circulating in the peritoneal fluid during stage III and stage IV (when patients are usually diagnosed) and lastly, cancer cells forming nodules at distant sites in the peritoneal cavity. The anti-mucin antibodies can be internalized through the process of endocytosis by the tumour cells, enabling the drug-loaded nanomicelles to gain entry and deliver the anti-neoplastic drugs inside the tumour cell, thus maintaining sustained and enhanced drug exposure to ovarian tumour cells. This targeting system can help reduce the tumour load responsible for adhesion at the sites of secondary metastasis (peritoneal and abdominal surfaces).

The nanomicelles are typically less than about 100 nm in diameter, and more typically between 20 and 100 nm. Nanomicelles of less than about 100 nm in diameter are optimal for deeper penetration into tumour nodules (Davis et al., 2008), substantiated by studies concluding that the pore size of most peripheral human tumours is approximately 200-600 nm in diameter (Monsky et al., 1999; Yuan et al., 1995). Nanomicelles of less than 100 nm have a unique core-shell architecture that protects drugs from degradation and inactivation, thereby increasing the amount of drug delivered to the tumour while reducing the characteristic side-effects of anti-neoplastic drugs (Trubetskov, 1999; Liu et al., 2006; Tong and Cheng, 2007; Matsumura, 2008). Hydrophobic aggregation in the interior environment of micelles can be stabilized by polyethylene glycol (PEG), which also provides a stable layer on the surface of the micelle, leading to prolonged circulation following intravenous injection and subsequent accumulation in ovarian tumours (Blume and Cevc, 1990; Pandey et al., 2002). By selecting specific combinations of polymers, the nanomicelles can be formed to be biodegradable, biocompatible, stable and have prolonged circulation of at least 24 hours or for superior stability, longer than 6 months in the peritoneum.

Suitable polymers for forming the pharmaceutical composition include polyethylene glycol (PEG), poly(vinyl alcohol), poly(dl-lactic acid) (PLA), poly(lactic-co-glycolic acid) (PLGA), poly(β-benzyl-aspartate) (PBLA), polycaprolactone (PCL), poly(γ-benzyl-1-glutamate) (PBLG), polylysine, polyaspartate P(Asp), poly(glutamic acid) P(Glu), poly(ethylene oxide) (PEO), polycaprolactone (PCL), poly(ethyleneimine) (PEI), poly(4-vinyl pyridine), poly(N-methyldietheneamine sebacate), maleimide, chitosan (CS), alginate, gellan gum, fibrin, collagen, gelatin, hyaluronic acid and dextran, or any combination thereof.

Reagents which can be used in manufacturing the pharmaceutical composition include 1-ethyl-3-(3-dimethylaminopropyl)carbodiimide (EDC), anhydrous toluene and chloroform ($CHCl_3$), deuterated chloroform (d-$CHCl_3$), dimethylsulfoxide (DMSO), ethyl ether, acetone, ethyl acetate, dichloromethane (DCM), dimethylformamide (DMF), methanol, methanesulfonic acid, sodium cholate (SC), poly(vinyl alcohol) (PVA), N,N-dicyclohexyl carbodiimide (DCC), N-hydroxysuccinimide (NHS) and bovine serum albumin (BSA).

The pharmaceutical composition of the present invention is a novel formulation which has not previously been described. It has the potential to:
- overcome the non-specific destruction of healthy tissue associated with conventional anti-neoplastic treatment and also reduce the development of multidrug-resistant tumours;
- provide superior selective accumulation of bioactives at the tumour site;
- reduce the likelihood of recurrence by controlling the release of bioactive-loaded targeting nanomicelles over an extended period of time;
- improve tumour tissue penetration and intracellular retention of anti-neoplastic drug to avoid P-glycoprotein efflux of the bioactives; and/or
- reduce the titer of malignant cells present in the peritoneum to reduce metastatic implantation.

These factors are likely to result in fewer side effects than current intraperitoneal therapy, improved patient compliance and/or an improved disease prognosis in ovarian cancer patients.

The invention will now be described in more detail by way of the following non-limiting examples.

EXAMPLES

Materials

Polymers used included: poly(β-benzyl-1-glutamate), polyethylene glycol (PEG), poly(vinyl alcohol) (Sigma-Aldrich, St. Louise, Mo., USA), poly(dl-lactic acid) (PLA), poly (lactic-co-glycolic acid) (PLGA), poly(β-benzyl-aspartate) (PBLA), polycaprolactone (PCL), poly(γ-benzyl-1-glutamate) (PBLG) (Resomer® RG504, Boehringer Ingelheim PharmKG, Ingelheim, Germany), polylysine, polyaspartate. P(Asp), poly(glutamic acid) P(Glu), poly(ethylene oxide) (PEO), polycaprolactone (PCL) (Union Carbide Corp., Danbury, Conn., USA), poly(ethyleneimine) (PEI), poly(4-vinyl pyridine), poly(N-methyldietheneamine sebacate), maleimide, chitosan (CS) (Food grade, Warren Chem Specialties, Johannesburg, South Africa), alginate (Protanal® LF10/60, FMC Biopolymer, Drammen, Norway), gellan gum (Kelcogel®, CP Kelco, Atlanta, USA), fibrin, collagen, gelatin, hyaluronic acid and dextran. Reagents used in this study are: 1-ethyl-3-(3-dimethylaminopropyl) carbodiimide (EDC) (Fluka), anhydrous toluene and chloroform (CHCl3) (Acros), deuterated chloroform (d-CHCl3), dimethylsulfoxide (DMSO) (Cambridge Isotope Laboratories), ethyl ether, acetone, ethyl acetate, dichloromethane (DCM), dimethylformamide (DMF), methanol (Fisher Scientific), Methanesulfonic acid, sodium cholate (SC), poly(vinyl alcohol) (PVA), N,N-dicyclohexyl carbodiimide (DCC), N-hydroxysuccinimide (NHS) and bovine serum albumin (BSA).

Characterization and Co-Polymer Synthesis of Nanomicelles

Polypeptide block and graft co-polymers from the above list were investigated for preparing cationic nanomicelles. The type of polymer and reaction conditions were manipulated in order to determine optimal parameters for the encapsulation of anticancer drugs. Grafted copolymers were synthesized using methanesulfonic acid as a solvent and catalyst for the potential formation of spherical nanomicelles with controllable sizes and positive zeta potentials that allow endocytosis by tumour cells. PEG or BSA were incorporated into nanomicelles to increase the stability of the formulation and confer a hydrophilic stearic barrier that increased intraperitoneal circulation time enabling nanomicelles to reach and target ovarian cancer cells. The hydrophobic inner core of the nanomicelles was formed by a complex of poly(β-benzyl-1-glutamate), P(Glu), PBLG and PEG into which the anti-neoplastic drugs such as paclitaxel (Tx), SN-38 (7-ethyl-10-hydroxy-camptothecin), carboplatin, oxaliplatin and ceramide were encapsulated.

Preparation of Fluorescent Nanomicelles and Drug Loading

Nanomicelles were doped with a hydrophobic Nile red fluorescence dye for detecting their in vitro surface binding and cell internalization by ovarian cancer cells. Anticancer drugs investigated included: paclitaxel (Tx), the most used anticancer agent (Cfm Oskar Tropitzsch, Marktredwitz, Germany), SN-38 (7-ethyl-10-hydroxy-camptothecin) (Sigma-Aldrich Chemie, Steinheim, Germany), carboplatin and oxaliplatin (cisplatin analogues used as standard drugs for ovarian cancer), and paclitaxel (Tx)-ceramide [co-therapy to overcome drug resistant human ovarian cancer cells (C2 and C6)] (C6-ceramide, Avanti Polar Lipids). The hydrophobic interactions (within the inner core of the nanomicelles) between the drug and the tri-block co-polymers (PBLA/G, PCL and PEG) aided in the encapsulation of the water-insoluble anti-neoplastic drugs. The quantity of drug incorporated into polymeric nanomicelles was determined by UV spectrophotometry (Cecil CE 3021, 3000 Series, Cecil Instruments, Cambridge, England). The drug encapsulation efficiency (DEE %) and drug loading (DL %) into nanomicelles was calculated as the percentage of drug entrapped in the nanomicelles with respect to the initial quantity of drug added in the formulation. The stability of the drug (against hydrolysis under physiological conditions) and the extended release was improved by adjusting the PCL content. Reverse-phase UPLC was used to evaluate the stability of anti-neoplastic drugs in nanomicelles. DSC analysis was performed to determine the physical state of entrapped drug and the thermal behaviour (melting peak) of the polymer after drug encapsulation. The particle sizes and zeta potentials of the nanomicelles before and after drug loading were analyzed by Zetasizer analysis (Zetasizer Nano ZS, Malvern Instruments, UK) and by scanning electron microscopy (SEM) (Phenom™ Desktop SEM, FEI Company, Oregon, USA) on gold-coated lyophilized samples (Balzers SCD 004 Sputter Coater). Photomicrographs were captured at various magnifications.

Antibody-Conjugation to Nanomicelles

An essential condition for optimal tumour targeting is the preservation of antibody immuno-reactivity and receptor specificity after coupling to the nanomicelles.

Humanized antibodies CA125 or OC125 for MUC16, CTM01 (also known as 7F11C7) or CMB-401 or EMA or CA15-3 for MUC1 and 1G8 for MUC4, were conjugated to drug-loaded nanomicelles. Nanomicelles were coated with either PEG or BSA for antibody conjugation. In brief, nanomicelles (2 mg) and 0.1 mL of 5% glutaraldehyde were added to 1 mL 4 mg/mL BSA solution in 0.1 mol/L PBS (pH 5.0). After stirring at 4° C. for 24 hours, the excess BSA was removed from the mixture by separation using a centrifuge, and the BSA-modified nanomicelles were dispersed in PBS and thereafter washed with PBS. The resulting nanomicelles were coupled to 20 μL antibodies (0.1 mg/mL in PBS) in the presence of 0.1 mL of 5% bi-functional crosslinker glutaraldehyde. The antibody-conjugated nanomicelles were then centrifuged, washed, suspended in 0.1 mol/L PBS buffer of pH 7.4, and stored in suspension at 4° C. before use. Alternatively, PEG was incorporated onto the surface of nanomicelles to provide a functional site for the surface conjugation of anti-mucin antibodies. Briefly, a 1 mL solution of antibodies recognizing MUC1, MUC4 and MUC16 was purified by centrifugation at 4000×g for 15 minutes (Centaur 2MSE) using Amicon Ultra-4 centrifugal filter devices. Purified antibody (2 mg) was activated in 1 mL of 0.1M PBS buffer (pH 7.5) by sonication and vortexing. Non-reacted antibodies were removed by centrifugation (4000×g for 15 minutes) using an Amicon Ultra-4 centrifugal filter device. MUC1, MUC4 and MUC16 activated antibodies (500 uL) were reacted for 1, 6 or 12 hours with gentle shaking at room temperature with 500 uL nanomicelle (20 mg/mL).

Hydrogel Fabrication and Encapsulation of the Nanomicelles

Co-polymers containing N-isopropylacrylamide (NIPAAM) (a temperature-sensitive monomer), 2-(dimethylamino)ethyl methacrylate (DMAEMA) and poly(methacrylic acid) (PMAA) (pH-sensitive monomers) were used to fabricate a dual-sensitive hydrogel that was stable before administration and swelled once introduced into the peritoneal environment to release the drug-loaded nanomicelles. The reversible swell-collapse transition modulated the release rate of the drug-loaded nanomicelles for controlled release. Proper materials selection, the fabrication process and surface texture was critical in formulating the biocompatible hydrogel component for controlled release of the drug-loaded nanomicelles. To eliminate the need for additional surgeries to recover the tri-block co-polymers PLA-PEG-PLA as well as chitosan, gelatin and dextran were used to design a biodegradable hydrogel. Chitosan was used to confer bio-adhesive properties to the hydrogel enabling it to adhere onto mucus membranes lining the peritoneal organs. The incorporation of drug-loaded nanomicelles was performed by mixing nanomicelles with the hydrogel polymer precursor solution.

In Vitro Drug Release Studies from the Nanomicelle

The in vitro systems were designed to include as many complexities of the in vivo environment (IP) as possible to accurately represent what may occur during the clinical application of the delivery system. To determine the influence of pH on the rate at which the hydrogel releases the drug-loaded nanomicelles, the in vitro drug release was carried out in HCl (pH 1.1), potassium acid phthalate buffered solution (pH 4.0-6.0, tumour environment), PBS with 0.1% Tween-80 (pH 7.4, to determine the release of chemo-drugs under neutral conditions) and sodium borate buffered saline solution (pH 10.0). The effect of temperature on the swelling of the hydrogel was evaluated by varying the temperature (23-40° C.) of the solutions used in the pH analysis studies. Drug release studies were performed for up to 5 days. Five milligrams of hydrogel containing the drug-loaded nanomicelles was dispersed in the dialysis tube filled with the test solution. The hydrogel was immersed in the dialysis (test) medium and at certain time intervals (24, 48, 72 and 96 hours), an aliquot (0.5 mL) of the dialysis medium was withdrawn, and the same volume of fresh medium was added. This test confirmed that the hydrogel encapsulating the drug-loaded nanomicelles was stable before administration and started to release the drug-loaded nanomicelles (the active component), under physiological conditions after administration.

Cell Culture Studies

Ovarian cancer cell lines used in this study were: OVCA433 or OVC429 or OVC432 or OVC424 or OVC400 or OVCAR-3 or Caov-3 (MUC16-expressing cell lines) (American Type Culture Collection ATCC, Manassas, Va.), A2780DDP and A2780 (MUC1-expressing cell lines resistant and sensitive to cisplatin respectively) (European Collection of Cell Cultures (Salisbury, UK), SKOV3 (drug sensitive) and SKOV3TR (multiple drug resistant) (MUC1 expressing cell lines) (Shanghai Cell Bank, China). Cells were cultured in RPMI 1640 (Gibco BRL, Paris, France) or (Mediatech, Inc.) and supplemented with 10% fetal bovine serum (FBS, HyClone, Logan, Utah), streptomycin (100 ug/mL) and penicillin (100 ug/mL) (Shanghai Cell Bank, China). The SKOV3TR sub-culture was maintained for MDR by the addition of 0.2 Amol/L paclitaxel in the culture medium. Cultures were maintained in a humidified, 5% $CO_2$ incubator at 37° C. and sub-cultured once or twice a week as needed.

In Vitro Cytotoxicity

To investigate whether the hydrogel, placebo and drug-loaded antibody bound nanomicelles and their degradation products could potentially act as cytotoxic agents, normal (non-malignant) ovarian cell lines were exposed to these molecules. In brief, viable cells (105/0.2 mL) were aliquoted into 15 mL test tubes containing 0.2 mL of the sample to be tested at the appropriate concentration (up to 2 mg/mL). Cells were then harvested and analyzed using a microplate reader (Model 550, Bio-RAD, Hercules, USA) at 595 nm. Treatment with serum-supplemented medium was used as a negative control (0% cell death), and treatment with 50 ug/mL poly (ethyleneimine) ($M_w$=10 kDa) was used as a positive control (100% cell death). Growth inhibition curves of each test sample were plotted, and the $IC_{50}$ value determined.

In Vitro Antibody-Bound Drug-Loaded Nanomicelles

Ovarian cancer cells were cultured until exponential phase when the growth medium was replaced by a fresh McCoy'5a medium supplemented with antibody-bound nanomicelles encapsulating a variety of anti-neoplastic drugs and incubated at 37° C. for 6 hours. After 1 hour incubation cells were washed three times with cold PBS and then incubated with fluorescein isothiocyanate (FITC)-conjugated Fab2 fragments of goat anti-mouse IgG (Dakopatts, Glostrup, Denmark) for a further 30 minutes at 48° C. Binding inhibition curves were plotted and the calculated $IC_{50}$ values for each conjugate were compared to the unmodified nanomicelle (not bound to antibody) as a relative measure of retention of immune-affinity. A stable compound formed between the antibody-conjugated-drug-loaded nanomicelles and the ovarian cancer cells were sputter-coated with a film of gold and analyzed by SEM.

Cell Internalization Studies

To quantitatively assess the intracellular application of antibody-bound-drug-loaded nanomicelles, the measurement of cell internalization by ovarian carcinoma cell-lines was conducted. Nile red-loaded nanomicelles (1 mg/mL) were added to culture medium and the ovarian cancer cells and incubated at 37° C. for the desired time. Nanomicelles that are bound to the outer plasma membrane of the ovarian cancer cells were released by exposure to isotonic pH 2.8 buffer, whereas internalized antibody-bound nanomicelles were not released. Fluorescence signals observed within the cytoplasm was an indication of successfully internalized Nile red-loaded nanomicelles. Attaching the fluorescent nanomicelle to internalizing antibodies such as MUC1, MUC4 and MUC16 helped to bypass normal membrane-based mechanisms of drug resistance, a very important application for intracellular drug delivery. After treatment, cells were stained for apoptosis.

In Vivo Induction of Ovarian or Peritoneal Tumours

Five female athymic mice (Nu/Nu strain) or female Balb/c nude mice, 4-6 weeks old, weighing 25 g, purchased from Charles River Laboratories (Cambridge, Mass.) were housed under controlled laboratory conditions in polycarbonate cages having free access to sterilized rodent pellet diet and acidified drinking water. To induce the formation of ovarian cancer in mice, approximately 8×106 human ovarian cancer cells bearing the MUC1, MUC4 and MUC16 tumour markers were injected into the peritoneal cavities of female athymic mice under light isoflurane anesthesia. The mice were monitored closely on a daily basis for signs of onset of the disease, and any other disease related illness. Treatment commenced when the mice developed ascites fluid in the peritoneal cavity and/or growth of solid tumours (approximately 8-12 weeks post inoculation) to a diameter of 10 mm in a single axis (using calipers). The tumours were visualized by a Vevo 2100 instrument for imaging tumours and were monitored on a daily basis to avoid tumour-related complications. Asymptomatic mice were euthanized 140 days subsequent to tumour inoculation. The mice were randomly allocated to different control and treatment groups.

In Vivo Tests for Anti-Tumour Activity

Ovarian-tumour-bearing female athymic mice (Nu/Nu strain) were divided into a control group, implanted (IP) with a hydrogel containing placebo, and two treatment groups: (1) IP injection (0.5 mL) of drug-loaded antibody-bound nanomicelles (2) IP implantation of the hydrogel encapsulating drug-loaded antibody-bound nanomicelles. Each group had five mice. Mice were anesthetized with ketamine (60 mg/kg) and xylazine (10 mg/kg). The hydrogel solution at room temperature was solidified upon injection into the peritoneum. This in situ sol-gel transition enabled surgery or implantation to be performed in a minimally invasive manner. Treatment commenced when the mice developed ascites fluid in the peritoneal cavity and/or growth of solid tumours (approximately 8-12 weeks post inoculation) to a diameter of 10 mm in a single axis (using calipers). The potential effectiveness of the implantable drug delivery system of the invention was compared against the control group and to confirm the probable effective dose. All procedures were carried out in accordance with the animal ethics guidelines of the University of the Witwatersrand. Therapeutic efficacy was evaluated by measuring the tumour diameters (twice weekly) and the changes in body weight as a function of time. The distribution of drug-loaded nanomicelles to tissues such as liver (a common site of therapeutic toxicity), spleen, lung, kidney and small intestine was evaluated. Regarding renal function, the plasma concentrations of creatinine were compared with that of the control group. On the day of the sacrifice, tumour bearing mice were imaged using the Vevo 2100 instrument (Micro Imaging Platform enhanced with the Cellvizio® Lab module by VisualSonics (Pty) Ltd).

Mathematical and Computational Modeling for Data Analysis

The controlled release of drug-loaded nanomicelles was modeled with software such as WinNonLin Version 5.1 (Pharsight software, USA) and Minitab® V14 (Minitab®, USA). The design supported an increase in release rate with decreasing pH values and increasing temperature. One of the unique challenges facing delivery systems is burst release, which may cause a "dose-dumping" effect that can be potentially fatal to patients in chemotherapy treatment. Material or drug interactions, fabrication conditions, and sample geometry and/or morphology are possible causes of burst release that were considered during the design of the hydrogel encapsulation drug-loaded nanomicelles.

Results and Discussion

Preliminary Computational Analysis for Formulation Blue-Printing

The 67-185 amino acid tandem repeat sequence of the SEA domain from murine hypothetical protein homologous to human mucin 16 MUC1 recognised as:

(SEQ ID NO: 1)
GSSGSSSGSSSSQHFNLNFTITNLPYSQDIAQPSTTKYQQTKRSIENALNQ
LFRNSSISYFSDCQVLAFRSVSNMNNHTGVDSLCNFSPLARRVDRVAIYE
EFLRMTHNGTQLLNFTLDRKSVFVDSGPSSG.

The sequence of antiMUC16 antibody consists of a heavy ($V_H$) and a light chain ($V_L$) having 119 and 106 amino acid residues, respectively. Each chain has some specific binding sites analogous to the MUC1 antigen known as complementarity determining region (CDRs).

Sulfhydryl-reactive (maleimide-activated) polyethylene glycol compounds with terminal methyl groups are often used to increase the residence time (×100) of antibodies in the plasma. They can also be used as a linker between antibody and effector molecule. PLLA can be used to conjugate amine drugs to its —COO groups to form an amide (CO—NH) linkage. MaleimidePEG-co-PLLA can be used to form the nanostructures. FIGS. 5 to 11 show the following computational model profiling of the cancer targeting pharmaceutical dosage form that was generated.

Figure 5:
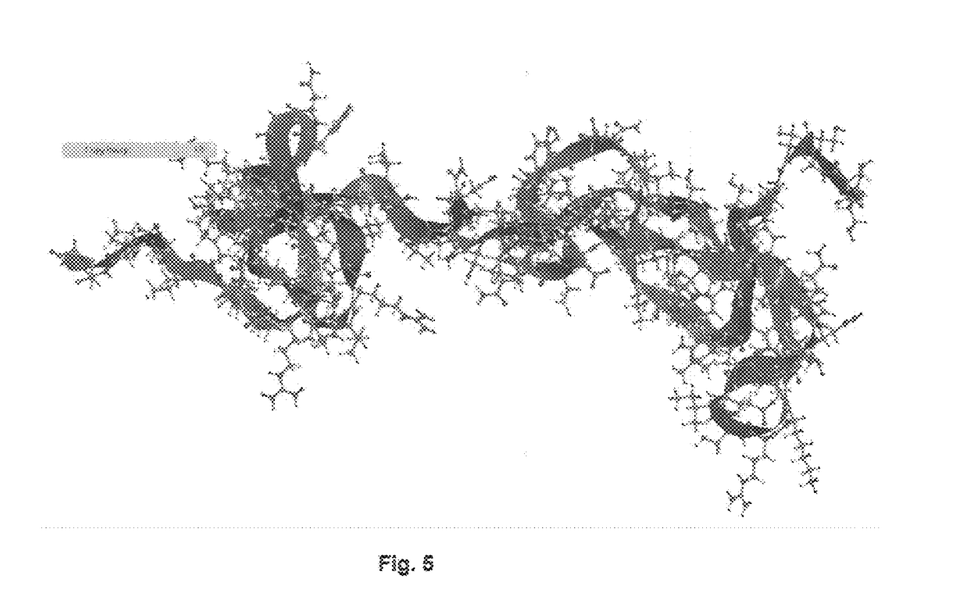
FIG. 5: shows the structure of protein homologous to human mucin 16 MUC1.
Figure 6:
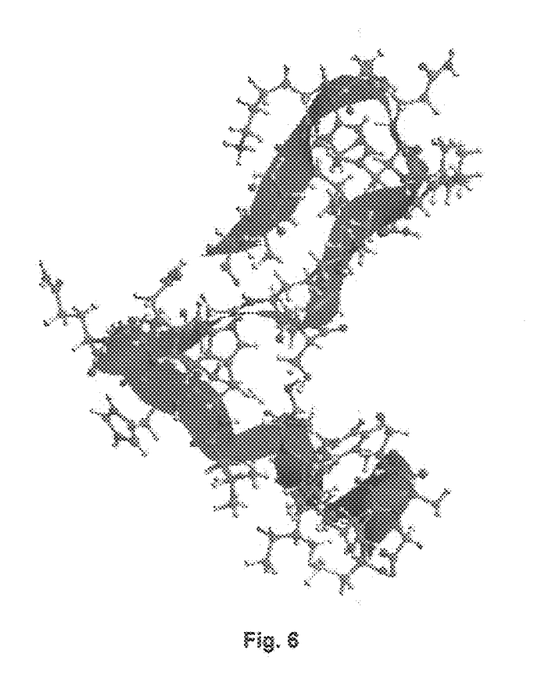
FIG. 6: shows an optimized structure of MUC16 antibody (Single-Chain Fragment of the Murine Anti-idiotypic Antibody ACA125) using a 35 amino acid chain: CQASENIYSY-LAWHQQKQG KSPQLLVYNAKTLAGG (SEQ ID NO: 16) having 2 CDRs.
Figure 7:
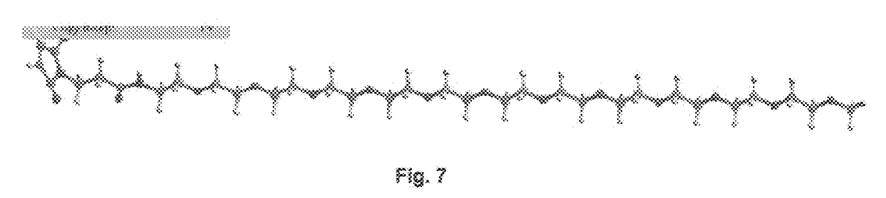
FIG. 7: shows an optimized structure of methoxy-PEG-Maleimide (MMPEG¬12)-chain length 12.
Figure 8:
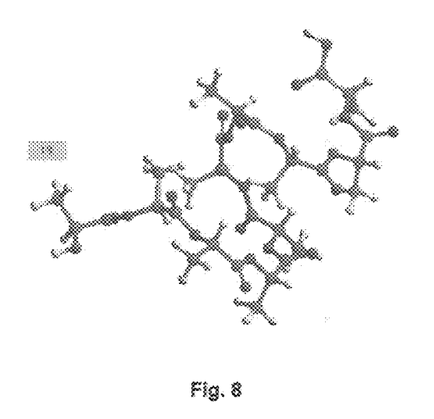
FIG. 8: shows an optimized structure of PLLA-chain length 10.
Figure 9:
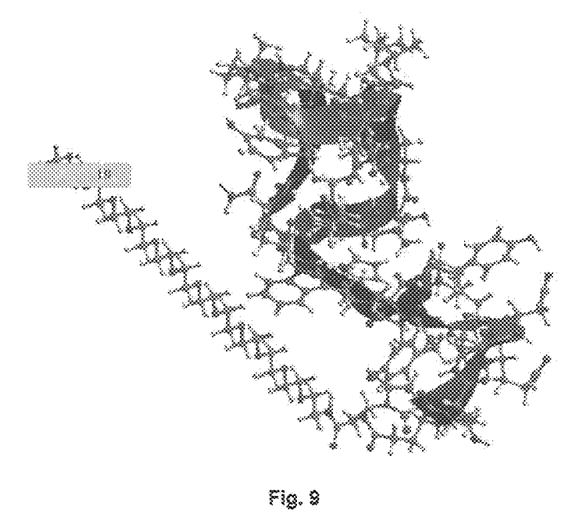
FIG. 9: shows a generated structure of MMPEG-conjugated-MUC1 antibody through the maleimide group and the sulphydryl group of cysteine.
Figure 10:
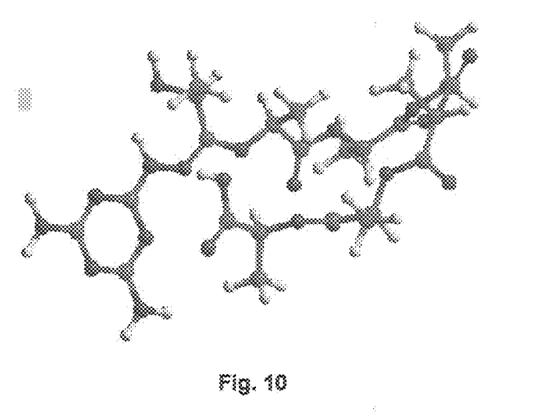
FIG. 10: shows altretamine (hexamethylmaleamine), a drug for ovarian cancer, conjugated with the PLLA through the amide linkage.
Figure 11:
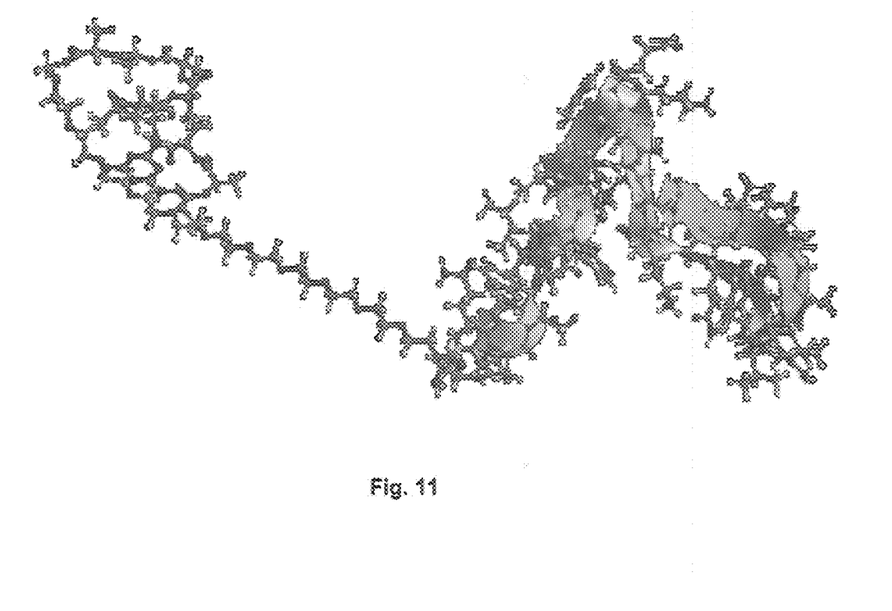
FIG. 11: shows an optimized structure of AntiMUC16 antibody-linked-MMPEG-co-PLLA-linked-altretamine.

1. The structure of protein homologous to human mucin 16 MUC1
2. Optimized the structure of MUC16 antibody (Single-Chain Fragment of the Murine Anti-idiotypic Antibody ACA125) using a 35 amino acid chain:

(SEQ ID NO: 16)
CQASENIYSYLAWHQQKQG KSPQLLVYNAKTLAGG
having 2 CDRs (underlined).

3. Optimized the structure of methoxy-PEG-Maleimide (MMPEG-12)-chain length
4. Optimized the structure of PLLA-chain length 10
5. Generated the structure of MMPEG-conjugated-MUC1 antibody through the maleimide group and the sulphydryl group of cysteine highlighted in bold in point 2.
6. Altretamine (hexamethylmaleamine), a drug for ovarian cancer, is conjugated with the PLLA through the amide linkage.
7. Finally optimized the structure of AntiMUC16 antibody-linked-MMPEG-co-PLLA-linked-altretamine.

The total energy value of MUC16 antibody-MMPEG-PLLA-drug of −382.27090 was relatively close to the optimised energy value of the MUC16 antibody of −444.42545. This implied that the tri-component guest system MM(PEG) 12-PLLA-drug complemented the conformational space of the host forming a thermodynamically stable complex.

REFERENCES

1. Armstrong D K, Bundy B, Wenzel L, Huang H Q, Baergen R, Lele S, Copeland, L. J., Walker, J. L., Burger, R. A., 2006. Intraperitoneal cisplatin and paclitaxel in ovarian cancer. New England Journal of Medicine. 354, 34-43.
2. Alberts D S, Liu P Y, Hannigan E V, O'Toole R, Williams S D, Young J A, Franklin, E. W., Clarke-Pearson, D. L., Malviya, V. K., DuBeshter, B., Adelson, M. D., Hoskins, W. J., 1996. Intraperitoneal cisplatin plus intravenous cyclophosphamide versus intravenous cisplatin plus intravenous cyclophosphamide for stage III ovarian cancer. New England Journal of Medicine. 35, 1950-1955.
3. Auersperg, N., Edelson, M. I., Mok, S. C., Johnson, S. W., Hamilton, T. C., 1998. The biology of ovarian cancer. Seminars in Oncology. 25, 281-304.
4. Auersperg, N., Wong, A. S, Choi, K. C., Kang, S. K., Leung, P. C., 2001. Ovarian surface epithelium: biology, endocrinology, and pathology. Endocrine Review. 22, 255-288.
5. Auersperg, N., Ota, T., Mitchell, G. W., 2002. Early events in ovarian epithelial carcinogenesis: progress and problems in experimental approaches. International Journal of Gynecological Cancer. 12, 691-703.
6. Belisle J A, Gubbels J A, Raphael C A, Migneault, M. A., Rancourt, C., Connor, J. P., Patankar, M. S., 2007. Peritoneal natural killer cells from epithelial ovarian cancer patients show an altered phenotype and bind to the tumour marker MUC16 (CA125). Immunology. 122, 418-429.
7. Bast, R. C., Feeney, M., Lazarus, H., Nadler, L. M., Colvin, R. B., Knapp, R. C., 1981. Reactivity of a monoclonal antibody with human ovarian carcinoma. Journal of Clinical Investigation. 68, 1331-1337.
8. Blume, G., Cevc, G., 1990. Liposomes for the sustained drug release in vivo. Journal of Biochemistry, Biophysics and Molecular Biology. 1029, 91-97.

TABLE 1

Molecular mechanic computations listing total AMBER energies and individual energy term contributions for minimized structures modelled

| Structure | Energy | | | | | | |
|---|---|---|---|---|---|---|---|
| | Total | Bond | Angle | Dihedral | VDW | H bond | Elec |
| MUC16 antibody | −444.42545 | 6.58055 | 55.3129 | 57.4766 | −83.8868 | −14.4239 | −465.485 |
| MM(PEG)$_{12}$ | 37.695597 | 0.428258 | 18.1439 | 12.7116 | 6.41447 | −0.00256 | 0 |
| PLLA | 1.713009 | 0.55997 | 5.62664 | 4.30817 | −8.77573 | −0.00605 | 0 |
| MUC16 antibody + MMPEG | −429.31572 | 7.35277 | 70.591 | 69.5583 | −89.8475 | −15.4952 | −471.475 |
| PLLA + drug | 3.932932 | 0.762945 | 5.82626 | 2.53346 | −4.87299 | −0.31674 | 0 |
| MM(PEG)12-PLLA + drug | 81.420378 | 1.60328 | 64.8421 | 26.0063 | −10.0378 | −0.99350 | 0 |
| MUC16 antibody-MMPEG-PLLA-drug | −382.27090 | 8.41232 | 116.709 | 85.7823 | −108.531 | −14.9454 | −469.698 |

VDW: van der waal's energy
Elec: electrostatic energy

9. Cannistra, S. A., 2004. Cancer of the Ovary. New England Journal of Medicine, 2004, 351, 2519-2529.
10. Cleare, M. J., Hydes, P. C., Malerbi, B. W., Watkins, D. M., 1978. Anti-tumour platinum complexes: relationships between chemical properties and activity. International Journal of Biochemistry and Molecular Biology. 60, 835-850.
11. Chauhan, S. C., Singh, A. P., Ruiz, F., Johansson, S. L., Jain, M., Smith, L. M., Moniaux, N., Batra, S. K., 2006. Aberrant expression of MUC4 in ovarian carcinoma: diagnostic significance alone and in combination with MUC1 and MUC16 (CA125). Modern Pathology 19, 1386-1394.
12. Daly, M., Obrams, G. I., 1998. Epidemiology and risk assessment for ovarian cancer. Seminars in Oncology. 25, 255-264.
13. Davis, M. E., Chen, Z. G., Shin, D. M., 2008. Nanoparticle therapeutics: an emerging treatment modality for cancer. Nature Reviews Drug Discovery. 7, 771-782.
14. Davidson, B., Baekelandt, M., Shih, I., 2007. MUC4 is upregulated in ovarian carcinoma effusions and differentiates carcinoma cells from mesothelial cells. Diagnostic Cytopathology. 35, 756-760.
15. Dong, Y., Walsh, M. D., 1997. Cummings M C, Wright R G, Khoo S K, Parsons P G, McGuckin M A: Expression of MUC1 and MUC2 mucins in epithelial ovarian tumours. Journal of Pathology. 183, 311-317.
16. Dreher, M. R., Liu, W., Michelich, C. R., Dewhirst, M. W., Yuan, F., Chilkoti, A., 2006. Tumour vascular permeability, accumulation, and penetration of macromolecular drug carriers. Journal of the National Cancer Institute. 98, 335-344.
17. du Bois, A., Luck, H. J., Meier, W., Adams, H. P., Mobus, V., Costa, S., Bauknecht, T., Richter, B., Warm, M., Schroder, W., Olbricht, S., Nitz, U., Jackisch, C., Emons, G., Wagner, U., Kuhn, W., Pfisterer, J., 2003. A randomized clinical trial of cisplatin/paclitaxel versus carboplatin/paclitaxel as first-line treatment of ovarian cancer. Journal of the National Cancer Institute. 95, 1320-1329.
18. Dubbelman, R., McVie, J. G., 1988. Pharmacokinetics of carboplatin after intraperitoneal administration. Cancer Chemotherapy and Pharmacology. 21, 57.
19. Feeley, K. M., Wells, M., 2001. Precursor lesions of ovarian epithelial malignancy. Histopathology. 38, 87-95.
20. Feldman, J. E., 1989. Ovarian failure and cancer treatment: incidence and interventions for premenopausal women. Oncology Nursing Forum 16, 651-657.
21. Friedlander, M. L., 1998. Prognostic factors in ovarian cancer. Seminars in Oncology. 25, 305-314.
22. Fritsche, H. A., Bast, R. C., 1998. CA 125 in ovarian cancer: advances and controversy. Clinical Chemistry. 44, 1379-1380.
23. Gendler, S., Lancaster, C., Taylor-Papadimitriou, J., Duhig, T., Peat, N., Burchell, J., Pemberton, L., Lalani, E. L. and Wilson, D. (1990) Molecular cloning and expression of the human tumour-associarted polymorphic epithelial mucin. Journal of Biological Chemistry. 265, 15286-15293.
24. Gendler, S. J., Spicer, A. P., 1995. Epithelial mucin genes. Annual Review of Physiology. 57, 607-634.
25. Giuntoli, R. L., Rodriguez, G. C., Whitaker, R. S., Dodge, R., Voynow, J. A., 1998. Mucin gene expression in ovarian cancers. Cancer Research. 58, 5546-5550.
26. Gubbels J A, Belisle J, Onda M, Rancourt, C., Migneault, M., Ho, M., Bera, T. K., Connor, J., Sathyanarayana, B. K., Lee, B., Pastan, I., Patankar, M. S., 2006. Mesothelin-MUC16 binding is a high affinity, N-glycan dependent interaction that facilitates peritoneal metastasis of ovarian tumours. Molecular Cancer. 5, 50.
27. Gubbels, J. A., Felder, M., Horibata, S., Belisle, J. A., Kapur, A., Holden, H., Petrie, S., Migneault, M., Rancourt, C., Connor, J. P., Patankar, M. S., 2010. MUC16 provides immune protection by inhibiting synapse formation between NK and ovarian tumour cells. Molecular Cancer. 9, 1-14.
28. Hankinson, S. E., Colditz, G. A., Hunter, D. J., Willett, W. C., Stampfer, M. J., Rosner, B., Hennekens, C. H., Speizer, F. E., 1995. A prospective study of reproductive factors and risk of epithelial ovarian cancer. Cancer 76, 284-290.
29. Hempling, R. E., Wong, C., Piver, M. S., Natarajan, N., Mettlin, C. J., 1997. Hormone replacement therapy as a risk factor for epithelial ovarian cancer: results of a case-control study. Obstetrics and Gynecology. 89, 1012-1016.
30. Hilgers, J., Zotter, S., Kenemans, P., 1988. Polymorphic epithelial mucin and CA125-bearing glycoprotein in basic and applied carcinoma research. Cancer Reviews 11-12:3-10, 1988
31. Hollingsworth, M. A., Strawhecker, J. M., Caffrey, T. C., Mack, D. R., 1994. Expression of MUC1, MUC2, MUC3 and MUC4 mucin mRNAs in human pancreatic and intestinal tumour cell lines. International Journal of Cancer. 57, 198-203.
32. Hollingsworth, M. A., Swanson, B. J., 2004. Mucins in cancer: protection and control of the cell surface. Nature Reviews Cancer. 4, 45-60.
33. Hoskins, W. J., McGuire, W P., Brady, M. F., Homesley, H. D., Creasman, W. T., Berman, M., Ball, H., Berek, J. S., 1994. The effect of diameter of largest residual disease on survival after primary cytoreductive surgery in patients with suboptimal residual epithelial ovarian carcinoma. American Journal of Obstetrics & Gynecology. 170, 974-979.
34. Jacobs, I. J., Oram, D. H., Bast, R. C., 1992. Strategies for improving the specificity of screening for ovarian cancer with tumour-associated antigens CA 125, CA 15-3, and TAG 72.3. Obstetrics and Gynecology. 80, 396-399.
35. Khayat, D., Antoine, E. C., Coeffic, D., 2000. Taxol in the management of cancers of the breast and the ovary. Cancer Investigation. 18, 242-260.
36. Kingsley, J. D., Dou, H., Morehead, J., Rabinow, B., Gendelman, H. E., Destache, C. J., 2006. Nanotechnology: a focus on nanoparticles as a drug delivery system. Journal of Neuroimmune Pharmacology. 1, 340-350.
37. Knauff, S., Urbach, G. I., 1977. Purification of human ovarian tumour-associated antigen and demonstration of circulating tumour antigen in patients with advanced ovarian malignancy. American Journal of Obstetrics and Gynecology. 127, 710-750.
38. Liu, J., Lee, H., Allen, C., 2006. Formulation of drugs in block copolymer micelles: drug loading and release. Current Pharmaceutical Design. 12, 4685-4701.
39. Lynch, H. T., Casey, M. J., Shaw, T. G., Lynch, J. F., 1998. Hereditary factors in gynecologic cancer. Oncologist. 3, 319-338.
40. MacGibbon, A., Bucci, J., MacLeod, C., Solomon, J., Dalrymple, C., Firth, I., Carter, J., 1999. Whole Abdominal Radiotherapy Following Second-Look Laparotomy For Ovarian Carcinoma. Gynecologic Oncology. 75, 62-67.
41. Maeda, H., Wu, J., Sawa, T., Matsumura, Y., Hori, K., 2000. Tumour vascular permeability and the EPR effect in macromolecular therapeutics: a review. Journal of Controlled Release. 65, 271-284.
42. Markman, M., Rowinsky, E., Hakes, T., Reichman, B., Jones, W., Lewis, J. L., Rubin, S., Curtin, J., Barakat, R., Phillips, M., 1992. Phase I trial of intraperitoneal taxol: a Gynecoloic Oncology Group study. Journal of Clinical Oncology. 10, 1485-1491
43. Markman, M., Walker, J. L., 2006. Intraperitoneal Chemotherapy of Ovarian Cancer: A Review, With a Focus on Practical Aspects of Treatment. Journal of Clinical Oncology. 24, 988-999.
44. Markman, M., Bundy, B. N., Alberts, D. S., Fowler, J. M., Clark-Pearson, D. L., Carson, L. F., Wadler, S., Sickel, J., 2001. Phase III trial of standard-dose intravenous cisplatin plus paclitaxel versus moderately high-dose carboplatin followed by intravenous paclitaxel and intraperitoneal cisplatin in small-volume stage III ovarian carcinoma: an intergroup study of the Gynecologic Oncology Group, Southwestern Oncology Group, and Eastern Cooperative Oncology Group. Journal of Clinical Oncology. 19, 1001-1007.
45. Matsumura, Y., 2008. Poly(amino acid) micelle nanocarriers in preclinical and clinical studies. Advanced Drug Delivery Reviews. 60, 899-914.
46. Menon, U., Jacobs, I., 2002. Screening for ovarian cancer. Best Practice and Research. Clinical Obstetrics and Gynaecology. 16, 469-482.
47. Monsky, W. L., Fukumura, D., Gohongi, T., Ancukiewcz, M., Weich, H. A., Torchilin, V. P., Yuan, F., Jain, R. K., 1999. Augmentation of transvascular transport of macromolecules and nanoparticles in tumours using vascular endothelial growth factor. Cancer Research. 59, 4129-4135.
48. Moore, R. G., Brown, A. K., Miller, M. C., Skates, S., Allard, W. J., Verch, T., Steinhoff, M., Messerlian, G., DiSilvestro, P., Granai, C. O., Bast, R. C., 2007. The use of multiple novel tumour biomarkers for the detection of ovarian carcinoma in patients with a pelvic mass. Gynecologic Oncology. 108, 402-408.
49. Murdoch, W. J., Van Kirk, E. A., Smedts, A. M., 2006. Complement-inhibiting effect of ovarian cancer antigen CA-125. Cancer Letters. 236, 54-57.
50. Order, S. E., J. Thurston, R. C., Kapp., 1975. Ovarian tumour antigens: a new potential for therapy. National Cancer Institute Monograph. 42, 33-43.
51. Ozols, R. F., Bookman, M. A., Connolly, D. C., Daly, M. B., Godwin, A. K., Schilder, R. J., Xu, X., Hamilton, T. C., 2004. Focus on epithelial ovarian cancer. Cancer Cell. 5, 19-24.
52. Ozols, R. F., Bookman, M. A., Young, R. C., 2006. Intraperitoneal chemotherapy for ovarian cancer. New England Journal of Medicine. 354, 1641-1642
53. Pandey, P. S, Rai, R., Singh, R. B., 2002. Synthesis of cholic acid-based molecular receptors: head-to-head cholaphanes. Journal of the Chemical Society Perkin Transactions. 1, 918-923.
54. Patankar, M. S., Jing, Y., Morrison, J. C., Belisle, J. A., Lattanzio, F. A., Deng, Y., Wong, N. K., Morris, H. R., Dell, A., Clark, G. F., 2005. Potent suppression of natural killer cell response mediated by the ovarian tumour marker CA125. Gynecologic Oncology. 99, 704-713.
55. Rose, M. R., Voynow, J. A., 2006. Respiratory Tract Mucin Genes and Mucin Glycoproteins in Health and Disease. Physiological Reviews. 86, 245-278.
56. Rossing, M. A., Daling, J. R., Weiss, N. S., Moore, D. E., Self, S. G., 1994. Ovarian tumours in a cohort of infertile women. New England Journal of Medicine. 331, 771-776.
57. Rowinsky, E. K., Donehower, R. C., 1995. Paclitaxel (taxol). New England Journal of Medicine. 332, 1004-1014.
58. Rump, A., Morikawa, Y., Tanaka, M., Minami, S., Umesak, N., Takeuchi, M., Miyajima, A., 2004. Binding of ovarian cancer antigen CA125/MUC16 to mesothelin mediates cell adhesion. Journal of Biological Chemistry. 279, 9190-9198.
59. Seiden, M. V., 2001. Ovarian cancer. Oncologist. 6, 327-332.
60. Sharma, A., Sharma, U.S., Straubinger, R. M., 1996. Paclitaxel-liposomes for intracavitary therapy of intraperitoneal P388 leukemia. Cancer Letters. 107, 265-272.
61. Skates S J, Horick N, Yu Y, Xu, F., Berchuck, A., Havrilesky, L. J., de Bruijn, H. W. A., van der Zee, G. J., Woolas, R. P., Jacobs, I. J., Zhang, Z., Bast, R. C., 2004. Preoperative sensitivity and specificity for early-stage ovarian cancer when combining cancer antigen CA-125II, CA 15-3, CA 72-4, and macrophage colonystimulating factor using mixtures of multivariate normal distributions. Journal of Clinical Oncology. 22, 4059-4066.
62. Stohlbach, L. A., Pitt, L., Gandhir, B., Dorsett, H., Barber, H., Iochim, H., 1979. Ovarian cancer patient antibodies and their relationship to ovarian cancer associated markers. In Compendium of Assays for Immunodiagnosis of Human Cancer, Elsevier North-Holland, Inc., New York. 553-557.
63. Singh, A. P., Moniaux, N., Chauhan, S. C., Meza, J. L., Batra, S. K., 2004. Inhibition of MUC4 expression suppresses pancreatic tumour cell growth and metastasis. Cancer Research. 64, 622-630.
64. Singh, A. P., Chaturvedi, P., Batra, S. K., 2007. Emerging roles of MUC4 in cancer: a novel target for diagnosis and therapy. Cancer Research. 67, 433-436.
65. Singh, A. P., Senapati, S., Ponnusamy, M. P., Jain, M., Lele, S. M., Davis, J. S., Steven Remmenga, S., Batra, S. K., 2008. Clinical potential of mucins in diagnosis, prognosis, and therapy of ovarian cancer. Lancet Oncology. 9, 1076-1085.
66. Swart, A. M. C., Burdett, S., Ledermann, J., Mook, P., and Parmar, M. K. B., 2008. Why i.p. therapy cannot yet be considered as a standard of care for the first-line treatment of ovarian cancer: a systematic review. Annals of Oncology. 19, 688-695.
67. Tamada, Y., Takeuchi, H., Suzuki, N., Susumu, N., Aoki, D., Irimura, T., 2007. Biological and therapeutic significance of MUC1 with sialoglycans in clear cell adenocarcinoma of the ovary. Cancer Science. 98, 1586-1591.
68. Tong, R., Cheng, J., 2007. Anticancer polymeric nanomedicines. Polymer Reviews. 47, 345-381.
69. Trimble, E., Berry, D., Gore, M., Kavanagh, J., Cohen, C., Pecorelli, S., Creasman, W., Mason, P., Heinz, P., 2003. Current Issues In The Design Of Ovarian Cancer Treatment Trials. Gynecologic Oncology. 88, 122-123.
70. Trubetskoy, V. S., 1999. Polymeric micelles as carriers of diagnostic agents. Advanced Drug Delivery Reviews. 37, 81-88.
71. Tsai, M., Lu, Z., Wang, J., Yeh, T. K., Wientjes, M. G., Au, J. L., 2007. Effects of carrier on disposition and antitumour activity of intraperitoneal paclitaxel. Pharmaceutical Research. 24, 1691-1701.
72. Unezaki, S., Maruyama, K., Hosoda, J., Nagai, I., 1996. Direct measurement of the extravasation of polyethylene glycol-coated liposomes into solid tumour tissue by in vivo fluorescence microscopy. International Journal of Pharmaceutics. 144, 11-17.
73. Weiss, R. B., Donehower, R. C., Wiernik, P. H., Ohnuma, T., Gralla, R. J., Trump, D L., Baker, J. R., Van Echo, D. A., Von Hoff, D. D., Leyland-Jones, B., 1990. Hypersensitivity reactions from taxol. Journal of Clinical Oncology. 8, 1263-1268.

74. Whitehouse, C., Solomon, E., 2003. Current Status of the Molecular Characterization of the Ovarian Cancer Antigen CA125 And Implications For Its Use In Clinical Screening. Gynecologic Oncology. 88, 152-157.

75. Yin, B. W., Dnistrian, A., Lloyd, K. O., 2002. Ovarian cancer antigen CA125 is encoded by the MUC16 mucin gene. International Journal of Cancer. 98, 737-740.

76. Yuan, F., Dellian, M., Fukumura, D., Leunig, M., Berk, D. A., Torchilin, V. P., Jain, R. K., 1995. Vascular permeability in a human tumour xenograft: molecular size dependence and cutoff size. Cancer Research. 55, 3752-3756.

77. Yusuf, R. Z., Duan, Z., Lamendola, D. E., Penson, R. T., Seiden, M. V., 2003. Paclitaxel resistance: molecular mechanisms and pharmacologic manipulation. Current Cancer Drug Targets. 3, 1-19.

The invention claimed is:

1. A pharmaceutical composition for the delivery of an anti-neoplastic agent to a human, the composition comprising:
   nanoparticles comprising
      an anti-neoplastic agent; and
      mucin antibodies,
   wherein the nanoparticles are embedded in a thermal- and pH-responsive hydrogel composition formed from N-isopropylacrylamide (NIPAAM) (a temperature-sensitive monomer), 2-(dimethylamino)ethyl methacrylate (DMAEMA) and poly(methacrylic acid) (PMAA) (pH-sensitive monomers), which is liquid at about ambient room temperature and in a solid or semi-solid form at body temperature and which swells in an acidic environment and thereby releases the nanoparticles,
   wherein the nanoparticles are nanomicelles formed from:
   (a) poly(β-benzyl-1-glutamate), poly(glutamic acid), poly(γ-benzyl-1-glutamate) and polyethylene glycol;
   (b) poly(β-benzyl-1-glutamate), poly(glutamic acid), poly(γ-benzyl-1-glutamate) and bovine serum albumin; or
   (c) poly(β-benzyl-1-glutamate), poly(glutamic acid), poly(γ-benzyl-1-glutamate), polyethylene glycol and bovine serum albumin.

2. The pharmaceutical composition according to claim 1, wherein the mucin antibodies are conjugated to the nanoparticles.

3. The pharmaceutical composition according to claim 1, wherein the antibodies are anti-MUC16 antibodies.

4. The pharmaceutical composition according to claim 1, wherein the antibodies are anti-MUC1 antibodies.

5. The pharmaceutical composition according to claim 1, wherein the antibodies are anti-MUC4 antibodies.

6. The pharmaceutical composition according to claim 3, wherein the anti-MUC16 antibodies are humanized antibodies OC125.

7. The pharmaceutical composition according to claim 4, wherein the anti-MUC1 antibodies are humanized antibodies CTM01 or CMB-401.

8. The pharmaceutical composition according to claim 5, wherein the anti-MUC4 antibodies are humanized antibodies 1 G8.

9. The pharmaceutical composition according to claim 1, wherein the anti-neoplastic agent is paclitaxel, SN-38 (7-ethyl-10-hydroxy-camptothecin), carboplatin, oxaliplatin, cisplatin, ceramide, calcheamicin or carboxyamido-triazole, or any combination thereof.

10. The pharmaceutical composition according to claim 1, wherein the nanomicelles are less than about 100 nm in diameter.

11. The pharmaceutical composition according to claim 1, wherein the hydrogel composition is additionally formed from chitosan, gelatine and/or dextran.

12. The pharmaceutical composition according to claim 1, which is in an injectible formulation.

13. The pharmaceutical composition according to claim 12, which is for injecting into the intraperitoneal cavity.

14. The pharmaceutical composition according to claim 1, wherein the anti-neoplastic agent is encapsulated in said nanoparticles.

15. The pharmaceutical composition according to claim 1, wherein the nanoparticles are nanomicelles formed from (a) poly(β-benzyl-1-glutamate), poly(glutamic acid), poly(γ-benzyl-1-glutamate) and polyethylene glycol.

16. The pharmaceutical composition according to claim 1, wherein the nanoparticles are nanomicelles formed from (b) poly(β-benzyl-1-glutamate), poly(glutamic acid), poly(γ-benzyl-1-glutamate) and bovine serum albumin.

17. The pharmaceutical composition according to claim 1, wherein the nanoparticles are nanomicelles formed from (c) poly(β-benzyl-1-glutamate), poly(glutamic acid), poly(γ-benzyl-1-glutamate), polyethylene glycol and bovine serum albumin, in addition to the antineoplastic agent.

18. A method of treating cancer in a human, the method comprising the step of: administering a therapeutically effective amount of the pharmaceutical composition according to claim 1 to the human.

19. The method according to claim 18, wherein:
the composition is injected into the human at a target site and forms a semi-solid hydrogel in response to the body temperature;
the hydrogel swells in response to the pH of the surrounding fluid and releases antibody-bound nanoparticles encapsulating at least one anti-neoplastic agent;
the nanoparticles specifically target mucin antigens on cancer cells; and
the anti-neoplastic agents are delivered into the targeted cancer cells.

20. The method according to claim 18, wherein the cancer is associated with aberrant mucin expression.

21. The method according to claim 20, wherein the cancer is ovarian, pancreatic, prostate, metastatic breast, bladder or lung cancer.

22. The method according to claim 21, wherein the cancer is ovarian cancer.

23. A method of manufacturing the pharmaceutical composition of claim 1, the method comprising the steps of:
encapsulating at least one anti-neoplastic agent within nanoparticles formed from (a), (b), or (c) of claim 1;
conjugating mucin antibodies to the nanoparticles; and
incorporating the antibody-bound nanoparticles into the biodegradable pH- and thermo-responsive hydrogel composition.

* * * * *

SEQUENCE LISTING

```
<160> NUMBER OF SEQ ID NOS: 16

<210> SEQ ID NO 1
<211> LENGTH: 131
<212> TYPE: PRT
<213> ORGANISM: Artificial Sequence
<220> FEATURE:
<223> OTHER INFORMATION: Synthetic peptide

<400> SEQUENCE: 1

Gly Ser Ser Gly Ser Ser Gly Ser Ser Ser Gln His Phe Asn Leu
1               5                   10                  15

Asn Phe Thr Ile Thr Asn Leu Pro Tyr Ser Gln Asp Ile Ala Gln Pro
             20                  25                  30

Ser Thr Thr Lys Tyr Gln Gln Thr Lys Arg Ser Ile Glu Asn Ala Leu
         35                  40                  45

Asn Gln Leu Phe Arg Asn Ser Ser Ile Ser Tyr Phe Ser Asp Cys Gln
     50                  55                  60

Val Leu Ala Phe Arg Ser Val Ser Asn Asn Asn His Thr Gly Val
65                  70                  75                  80

Asp Ser Leu Cys Asn Phe Ser Pro Leu Ala Arg Arg Val Asp Arg Val
                85                  90                  95

Ala Ile Tyr Glu Glu Phe Leu Arg Met Thr His Asn Gly Thr Gln Leu
            100                 105                 110

Leu Asn Phe Thr Leu Asp Arg Lys Ser Val Phe Val Asp Ser Gly Pro
        115                 120                 125

Ser Ser Gly
    130

<210> SEQ ID NO 2
<211> LENGTH: 30
<212> TYPE: PRT
<213> ORGANISM: Artificial Sequence
<220> FEATURE:
<223> OTHER INFORMATION: Synthetic peptide

<400> SEQUENCE: 2

Gln Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr
            20                  25                  30

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Asn Val Trp Met Gln
1               5
```

```
<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Trp Val Lys Gln Arg Pro Gly Gln Gly Leu Asp Trp Ile Gly
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide

<400> SEQUENCE: 5

Ala Phe Tyr Pro Gly Asp Gly Asn Thr Arg Tyr Thr His Lys Phe Lys
1               5                   10                  15

Gly

<210> SEQ ID NO 6
<211> LENGTH: 32
<212> TYPE: PRT
<213> ORGANISM: Artificial Sequence
<220> FEATURE:
<223> OTHER INFORMATION: Synthetic peptide

<400> SEQUENCE: 6

Lys Ala Thr Leu Thr Ala Asp Lys Ser Ser Thr Ala Tyr Met Gln
1               5                   10                  15

Leu Ser Ser Leu Ala Ser Glu Asp Ser Gly Val Tyr Tyr Cys Ala Arg
            20                  25                  30

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Gly Glu Gly Asn Tyr Ala Trp Phe Ala Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Trp Gly Gln Gly Thr Thr Val Thr Val Ser Ser
1               5                   10

<210> SEQ ID NO 9
<211> LENGTH: 23
<212> TYPE: PRT
<213> ORGANISM: Artificial Sequence
<220> FEATURE:
<223> OTHER INFORMATION: Synthetic peptide
```

```
<400> SEQUENCE: 9

Asp Ile Glu Leu Thr Gln Ser Pro Ala Ser Leu Ser Ala Ser Val Gly
1               5                   10                  15

Glu Thr Val Thr Ile Thr Cys
            20

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Gln Ala Ser Glu Asn Ile Phe Ser Tyr Leu Ala
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Trp His Gln Gln Lys Gln Gly Lys Ser Pro Gln Leu Leu Val Tyr
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Asn Ala Lys Thr Leu Ala Gly
1               5

<210> SEQ ID NO 13
<211> LENGTH: 32
<212> TYPE: PRT
<213> ORGANISM: Artificial Sequence
<220> FEATURE:
<223> OTHER INFORMATION: Synthetic peptide

<400> SEQUENCE: 13

Gly Val Ser Ser Arg Phe Ser Gly Ser Gly Ser Gly Thr His Phe Ser
1               5                   10                  15

Leu Lys Ile Lys Ser Leu Gln Pro Glu Asp Phe Gly Ile Tyr Tyr Cys
            20                  25                  30

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Gln His His Tyr Gly Ile Leu Pro Thr
1               5

<210> SEQ ID NO 15
<211> LENGTH: 11
```

```
<212> TYPE: PRT
<213> ORGANISM: Artificial Sequence
<220> FEATURE:
<223> OTHER INFORMATION: Synthetic peptide

<400> SEQUENCE: 15

Phe Gly Gly Gly Thr Lys Leu Glu Ile Lys Arg
1               5                   10

<210> SEQ ID NO 16
<211> LENGTH: 35
<212> TYPE: PRT
<213> ORGANISM: Artificial Sequence
<220> FEATURE:
<223> OTHER INFORMATION: Synthetic peptide

<400> SEQUENCE: 16

Cys Gln Ala Ser Glu Asn Ile Tyr Ser Tyr Leu Ala Trp His Gln Gln
1               5                   10                  15

Lys Gln Gly Lys Ser Pro Gln Leu Leu Val Tyr Asn Ala Lys Thr Leu
            20                  25                  30

Ala Gly Gly
        35
```